(12) United States Patent
Yeh (10) Patent No.: US 12,303,584 B2
(45) Date of Patent: May 20, 2025

(54) SKINCARE COOLING PRODUCT, METHOD OF MAKING, AND METHOD OF USING THE SAME

(71) Applicant: EZTIA CORP., Diamond Bar, CA (US)

(72) Inventor: Tiffany Yeh, Diamond Bar, CA (US)

(73) Assignee: EZTIA CORP, Diamond Bar, CA (US)

( * ) Notice: Subject to any disclaimer, the term of this patent is extended or adjusted under 35 U.S.C. 154(b) by 0 days.

(21) Appl. No.: 18/910,243

(22) Filed: Oct. 9, 2024

(65) Prior Publication Data
US 2025/0032394 A1  Jan. 30, 2025

Related U.S. Application Data

(63) Continuation of application No. PCT/US2023/036081, filed on Oct. 27, 2023.
(Continued)

(51) Int. Cl.
*A61K 8/81* (2006.01)
*A61K 8/02* (2006.01)
(Continued)

(52) U.S. Cl.
CPC .......... *A61K 8/8158* (2013.01); *A61K 8/0212* (2013.01); *A61K 8/042* (2013.01);
(Continued)

(58) Field of Classification Search
CPC ...... A61K 9/0014; A61K 47/10; A61K 47/38; A61K 9/06; A61K 2800/524; A61K 31/215; A61K 47/02; A61K 47/183; A61K 47/32; A61K 9/08; A61K 8/345; A61K 31/19; A61K 31/20; A61K 8/34; A61K 8/342; A61K 8/37; A61K 8/44; A61K 31/09; A61K 31/14; A61K 33/40; A61K 8/042; A61K 8/347; A61K 8/416; A61K 8/43; A61K 8/4926; A61K 8/73; A61K 8/731; A61K 8/8147; A61K 2800/10; A61K 2800/262; A61K 2800/51; A61K 2800/70; A61K 2800/805; A61K 31/08; A61K 31/221; A61K 31/4164; A61K 31/4172; A61K 47/14; A61K 8/0208; A61K 8/19; A61K 8/27; A61K 8/365; A61K 8/375; A61K 8/39; A61K 8/41; A61K 8/492; A61K 8/4946; A61K 8/735; A61K 8/86; A61K 8/92; A61K 9/70; A61K 31/22; A61K 31/74; A61K 31/785; A61K 33/38; A61K 36/355; A61K 47/26; A61K 47/34; A61K 8/9789; A61K 8/9794; A61K 9/1273; A61K 9/5153; A61K 47/6849; A61K 9/0019; A61K 31/343; A61K 38/1841; A61K 38/2013; A61K 47/24; A61K 47/40; A61K 47/58; A61K 47/6937; A61K 47/6951; A61K 9/127; A61K 9/1271; A61K 9/1277; A61K 47/36; A61K 2035/128; A61K 35/12; A61K 35/36; A61K 35/39; A61K 38/02; A61K 9/0051; A61K 9/0009; A61K 9/0024; A61K 9/006; A61K 2800/244; A61K 2800/87; A61K 8/0212; A61K 8/20; A61K 8/23; A61K 8/733; A61K 8/8158; A61K 9/0048; A61K 9/5036; A61K 9/5146; A61K 9/7007; A61K 2800/54; A61K 2800/5422; A61K 2800/5424; A61K 6/69; A61K 8/22; A61K 8/8152; A61K 8/817; A61K 8/8176; A61K 9/0056; A61K 9/7023; A61K 2800/413; A61K 2800/621; A61K 2800/622; A61K 2800/624; A61K 2800/81; A61K 31/155; A61K 31/196; A61K 31/445; A61K 38/16; A61K 38/18; A61K 41/0052; A61K 41/0057; A61K 45/06; A61K 47/60;
(Continued)

(56) References Cited

U.S. PATENT DOCUMENTS

2003/0167556 A1* 9/2003 Kelley ................ A45D 44/002
                                                          2/206
2009/0110732 A1* 4/2009 Jabbari ................ A61K 31/765
                                                          977/773
(Continued)

FOREIGN PATENT DOCUMENTS

CN          210472144 U   *  5/2020  ............... A61B 5/08

OTHER PUBLICATIONS

CN210472144U translation (Year: 2020).*

Primary Examiner — Audrea B Coniglio
Assistant Examiner — Audrea Buckley
(74) Attorney, Agent, or Firm — Duane Morris LLP (57) ABSTRACT

A skincare product, a pack comprising such a skincare product, methods of making the skincare product and the pack, and a method of using the skincare product are provided. Such a skincare product is configured to provide skincare and cooling and comprises a hydrogel layer. The hydrogel layer comprises at least 50% of a liquid portion based on a total weight of the hydrogel layer, and a solid gel portion. The solid gel portion comprises moieties of an acrylamide as a monomer, a bisacrylamide as a crosslinker, a moisture absorbing agent, and an antimicrobial agent. The liquid portion comprises water and is water, a toning water, or an essence water. The liquid portion is embedded and distributed within the solid gel portion. The hydrogel layer has covalent crosslinks as a single type of crosslinking structure.

19 Claims, 2 Drawing Sheets

Related U.S. Application Data (60) Provisional application No. 63/482,604, filed on Feb. 1, 2023.

(51) Int. Cl.

| | | |
|---|---|---|
| *A61K 8/04* | (2006.01) | |
| *A61K 8/23* | (2006.01) | |
| *A61K 8/27* | (2006.01) | |
| *A61K 8/73* | (2006.01) | |
| *A61Q 17/00* | (2006.01) | |
| *A61Q 19/00* | (2006.01) | |

(52) U.S. Cl.
CPC .................. *A61K 8/23* (2013.01); *A61K 8/27* (2013.01); *A61K 8/733* (2013.01); *A61Q 17/005* (2013.01); *A61Q 19/00* (2013.01); *A61K 2800/244* (2013.01)

(58) Field of Classification Search
CPC ............. A61K 47/6903; A61K 8/0225; A61K 8/0241; A61K 8/0245; A61K 8/0283; A61K 8/11; A61K 8/29; A61K 9/0043; A61K 9/0046; A61K 9/0063; A61K 9/0085; A61K 9/009; A61K 9/1075; A61K 9/1617; A61K 9/1652; A61K 9/1682; A61K 9/19; A61K 9/5115; A61K 9/5123; A61K 9/7046; A61K 9/7084; A61K 2039/5252; A61K 2039/543; A61K 2039/55505; A61K 2039/55583; A61K 2039/70; A61K 31/7088; A61K 38/00; A61K 38/1825; A61K 38/2026; A61K 38/43; A61K 39/05; A61K 39/12; A61K 39/39; A61K 40/17; A61K 40/22; A61K 40/24; A61K 40/416; A61K 47/643; A61K 47/6927; A61K 49/14; A61K 49/1821; A61K 49/1896; A61K 9/1635; A61K 9/1647; A61K 9/1658; A61K 9/20; A61K 9/48; A61K 9/5052; A61K 9/5068; A61K 9/7053; A61K 9/7061; A61K 9/7069

See application file for complete search history.

(56) References Cited

U.S. PATENT DOCUMENTS

2016/0185712 A1\* 6/2016 Casasanta, III ....... C07C 233/20
                                                                    525/50
2018/0244858 A1\* 8/2018 Illeperuma ............... C08K 3/22

\* cited by examiner

SKINCARE COOLING PRODUCT, METHOD OF MAKING, AND METHOD OF USING THE SAME

PRIORITY CLAIM AND CROSS-REFERENCE

This application is a continuation of International Application No. PCT/US2023/036081, filed Oct. 27, 2023, which claims the priority benefit of U.S. Provisional Application No. 63/482,604, filed Feb. 1, 2023, which application is expressly incorporated by reference herein in its entirety.

FIELD OF THE INVENTION

The disclosure relates to a skincare product generally. More particularly, the disclosed subject matter relates to a skincare product such as a mask, a pad or a patch configured to contact and clean or treat skin of a subject in need such as a human and also provide a cooling effect.

BACKGROUND

A cosmetic facial mask prepared by impregnating a cosmetic liquid such as a skin lotion into a nonwoven fabric has been used. The mask has capability of simple use, a high beautification effect, and high mental satisfaction to a user.

Some purposes of using a cosmetic facial mask may include moisturizing, skin texture conditioning, care of tension and sagging, care of a wrinkle and a ripple, make-up sitting improvement, skin-pore tightening, and skin tightening. So the cosmetic facial mask is used not only as a moisturizing tool but also as a functional cosmetic material for tension and sagging, wrinkle and ripple caring, and skin tightening.

Cooling skin or an injury site of a subject in need, for example, using ice, is performed. Sometimes cooling skin may provide soothing effect. Cooling of an injury site after injury is important in reducing the swelling and inflammation around the site of injury and speeding recovery. After the acute phase has passed, recovery is often aided by episodes of heating. Athletes have also learned about the importance of using cooling to assist in recovery after training. Cooling reduces pain, reduces tissue damage and has also been shown to have a positive effect on performance.

Active cooling uses electricity to power a coolant, whether it's water or air, to dissipate heat from a surface.

Alginate-acrylamide hydrogel has a double network structure, which may have covalent crosslinks and ionic crosslinks. See e.g., A. Pragya, et al., "Dynamic crosslinking of an alginate-acrylamide tough hydrogel system: time-resolved in situ mapping of gel self-assembly," *RSC Adv.* 2021, 11, 10710. Composite materials including alginate-acrylamide based dual network hydrogel have also been explored for cooling uses. See P. Gogoi, et al., "Ductile cooling phase change material," *Nanoscale Adv.*, 2020, 2, 3900; International Application WO 2021/178601.

SUMMARY

The present disclosure provides a skincare product, a method of making the skincare product, and a method of using the skincare product. Such a skincare product may be in a form including, but not limited to a mask, a pad, a patch, a film or any combination thereof. The skincare product also provides a cooling effect on skin. The skincare product such as a facial mask and a neck patch or pad has one-layer structure in some embodiments and is configured to contact and treat skin of a subject such as a human being while also providing cooling effect.

In one aspect, the present disclosure provides a skincare product configured to provide skincare and cooling. Such a skincare product comprises a hydrogel layer, which comprises at least 50% of a liquid portion based on a total weight of the hydrogel layer, and a solid gel portion. The solid gel portion comprises moieties of an acrylamide as a monomer, a bisacrylamide as a crosslinker, a moisture absorbing agent, and an antimicrobial agent. The liquid portion comprises water. The liquid portion is water, a toning water, an essence water, or a combination thereof. The liquid portion is embedded and distributed within the solid gel portion. The hydrogel layer has covalent crosslinks as a single type of crosslinking structure. In some embodiments, no ionic crosslinks exist in the hydrogel layer.

In some embodiments, the hydrogel layer has a single-layer structure, and the skincare product is in a form selected from the group consisting of a mask (such as a facial mask), a pad, a patch, and any combination thereof.

Examples of a suitable moisture absorbing agent (or desiccator) include, but are not limited to, calcium sulfate, calcium chloride, potassium chloride, any hydrates thereof, and any combination thereof. Examples of a suitable antimicrobial agent include, but are not limited to zinc oxide, titanium oxide, and any combination thereof.

In some embodiments, the solid gel portion comprises 50%-80% of the moieties of the acrylamide, 0.1%-1% of the moieties of the bisacrylamide, 0.1%-20% of the moisture absorbing agent, and 0.1%-25% of the antimicrobial agent, based on a total weight of the solid gel portion on a dry weight basis.

In some embodiments, the solid gel portion further comprises moieties from an initiator in a range of from 1% to 8% and an accelerator in a range of from 0.1% to 1%, based on a total weight of the solid gel portion on a dry weight basis. For example, in some embodiments, the initiator is ammonium persulfate (APS) and the accelerator is N,N'-methylenebis(acrylamide) (MBAA).

In some embodiments, the hydrogel layer comprises 80% to 95% such as 80%-86% by weight of the liquid portion.

In accordance with some embodiments, a skincare product, which is configured to provide skincare and cooling, comprises a hydrogel layer. The hydrogel comprises 50%-95% of a liquid portion based on a total weight of the hydrogel layer, and a solid gel portion. The solid gel portion consists essentially of moieties of an acrylamide as a monomer, a bisacrylamide as a crosslinker, an initiator, an accelerator, a moisture absorbing agent, and an antimicrobial agent. Each ingredient is described herein. In some embodiments, the hydrogel layer comprises 80% to 95% such as 80%-86% by weight of the liquid portion.

The liquid portion comprises water and is selected from a group consisting of water, a toning water, an essence water, or a combination thereof. The liquid portion is embedded and distributed within the solid gel portion. The hydrogel layer has covalent crosslinks as a single type of crosslinking structure. The hydrogel layer has a single-layer structure, and the skincare product has no other layer in addition to the hydrogel layer. The hydrogel layer is configured to be applied directly to skin of a subject such as a human being (e.g., a woman).

In some embodiments, the moisture absorbing agent is selected from the group consisting of calcium sulfate, calcium chloride, potassium chloride, any hydrates thereof, and any combination thereof. The antimicrobial agent is selected from the group consisting of zinc oxide, titanium oxide, and any combination thereof. In some embodiments, the initiator is ammonium persulfate (APS) and the accelerator is N,N'-methylenebis(acrylamide) (MBAA).

The base polymer in the hydrogel layer is polyacrylamide (PAM). No other base ingredient such as alginate (e.g., calcium alginate or sodium alginate) for a dual network hydrogel is used. In some embodiments, in addition to one type of polyacrylamide, the hydrogel does not include poly(N-isopropylacrylamide) (PNIPAM), polyvinyl alcohol (PVA) or other base polymers for forming a dual network. Poly(N-isopropylacrylamide) (PNIPAM) by itself may be used.

In some embodiments, the solid gel portion comprises 50%-80% of the acrylamide, 0.1%-1% of the bisacrylamide, 1%-8% of the initiator, 0.1% to 1% of the accelerator, 0.1%-20% of the moisture absorbing agent, and 0.1%-25% of the antimicrobial agent, based on corresponding moieties and a total weight of the solid gel portion on a dry weight basis.

The hydrogel layer has any suitable thickness, for example, in a range of from 0.5 mm to 1 cm (e.g., from 1 mm to 10 mm).

In another aspect, the present disclosure provides a pack or container (or called packed product) comprising an enclosure and the skin skincare product enclosed therein. The skincare product as described herein is disposed inside the enclosure. The enclosure may be a plastic bag, a paper bag coated with a plastic layer, plastic film, plastic box, glass box, or any combination thereof. Such a skincare product may be in a form including, but not limited to a mask, a pad, a patch, a film or any combination thereof. The skincare product is reusable.

In another aspect, the present disclosure provides a method of making the skincare product as described herein. The method comprises the steps of making each component and combining together to form the skincare product. Such a method comprises mixing at least two portions of sols as described herein. The present disclosure provides a method of making the packed product as described herein. The present disclosure also provides a method of using the skincare product as described herein.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" refer to a relationship wherein structures are secured or attached to one another either directly or indirectly through intervening structures, as well as both movable or rigid attachments or relationships, unless expressly described otherwise.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure, the singular forms "a," "an," and "the" include the plural reference, and reference to a particular numerical value includes at least that particular value, unless the context clearly indicates otherwise. Thus, for example, a reference to "a nano structure" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to +10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The term "hydrogel" used herein refers to a gel which includes a water-insoluble, three-dimensional network of polymer chains capable of holding large amounts of water. The polymer or polymers therein may include ionic, covalent, or both ionic and covalent crosslinking structure. A compound comprising ions and/or a curative as a crosslinker may be used to form crosslinks in the polymer or polymers, which are generally hydrophilic. The hydrogel is highly absorbent and also has good mechanical properties.

The term "double network hydrogel" used herein refers to a hydrogel having two types of crosslinks, for example, both covalent and ionic crosslinks. Such a double network hydrogel has interpenetrating network (IPN) structure.

The term "single network hydrogel," "mono-network hydrogel," or "singular network hydrogel" used herein refers to a hydrogel have only one single type of crosslinks, for example, covalent crosslinks only without ionic crosslinks. The hydrogel disclosed in the present disclosure is a single network hydrogel.

The present disclosure provides a skincare product, a packed product comprising the skincare product, a method of making the skincare product, a method of making the packed product, and a method of using the skincare product. Such a skincare product may be in a form including, but not limited to a mask, a pad, a patch, a film or any combination thereof. The skincare product also provides a cooling effect on skin. The skincare product such as a facial mask and a neck patch or pad has one-layer structure, and is configured to contact and treat skin of a subject such as a human being while also providing cooling effect.

In accordance with some embodiments, a skincare product provided herein is configured to provide skincare and cooling. Such a skincare product comprises a hydrogel layer. Such a hydrogel layer comprises at least 50% of a liquid portion based on a total weight of the hydrogel layer, and a solid gel portion. The solid gel portion comprises moieties of an acrylamide as a monomer, a bisacrylamide as a crosslinker, a moisture absorbing agent, and an antimicrobial agent. The liquid portion comprises water, and is water, a toning water, an essence water, or any combination thereof. The liquid portion is embedded and distributed within the solid gel portion. The hydrogel layer has covalent crosslinks as a single type of crosslinking structure. In some embodiments, no ionic crosslinks exist in the hydrogel layer.

The liquid portion comprising water may be in any amount even though at least 50% is preferred. The hydrogel may have less water and may be soaked in water to increase water content before use. For example, the content of the liquid portion may be in a range of 50%-95%, 50%-90%, 60%-95%, 70%-95%, or 80%-95%. In some embodiments, the hydrogel layer comprises 80% to 86% (e.g., 84-86%) of the liquid portion based on the weight of liquid portion in the total weight of the hydrogel.

In some embodiments, the hydrogel layer has a single-layer structure, and the skincare product is in a form selected from the group consisting of a mask (such as a facial mask), a pad, a patch, and any combination thereof.

In some embodiments, the skincare product is reusable skincare mask or pad that can be made into different shapes to cool a body part such as a face or neck. The mask is a single-layer polyacrylamide hydrogel with the additives such as calcium sulfate, calcium chloride, or potassium chloride as desiccants that enhance cooling performance; zinc oxide or titanium dioxide for antimicrobial properties; and facial toning or essence water for skincare benefits.

The facial toning or essence water can be customized to confer different benefits and may comprise ingredients including, but not limited to, glycerin, agar, xanthan gum, carrageenan, carob gum, cellulose gum, hydrolyzed collagen, hyaluronic acid, potassium sorbate, sucrose, glucose, inositol, disodium EDTA, 1,2-hexanediol, allantoin, polyglyceryl-10 laurate, butylene glycol, dipropylene glycol, and any combination thereof.

When applied to the face and neck, the skincare product provided in this disclosure reduces skin temperature up to 8.5° C., and the cooling effect and adherence last up to 90 minutes.

Examples of a suitable moisture absorbing agent (or desiccator) include, but are not limited to, calcium sulfate, calcium chloride, potassium chloride, any hydrates thereof, and any combination thereof. Examples of a suitable antimicrobial agent include, but are not limited to zinc oxide, titanium oxide, and any combination thereof.

In some embodiments, the solid gel portion comprises 50%-80% of the moieties of the acrylamide, 0.1%-1% of the moieties of the bisacrylamide, 0.1%-20% of the moisture absorbing agent, and 0.1%-25% of the antimicrobial agent, based on a total weight of the solid gel portion on a dry weight basis.

For example, the content of the moisture absorbing agent is in a range of 1%-18%, for example, 9%-18%, based on a total weight of the solid gel portion on a dry weight basis. The content of the antimicrobial agent may be in a range of 1%-25%, 1%-20%, 2%-25%, 5%-25%, or any other suitable ranges, based on a total weight of the solid gel portion on a dry weight basis.

In some embodiments, the solid gel portion further comprises moieties from an initiator in a range of from 1% to 8% (e.g., 3%-8%) and an accelerator in a range of from 0.1% to 1% (e.g., 0.1%-0.5%), based on a total weight of the solid gel portion on a dry weight basis. For example, in some embodiments, the initiator is ammonium persulfate (APS) and the accelerator is N,N'-methylenebis(acrylamide) (MBAA).

In accordance with some embodiments, a skincare product is configured to provide skincare and cooling and comprising a hydrogel layer, which comprises 50%-95% (e.g., 80%-86%) of a liquid portion based on a total weight of the hydrogel layer, and a solid gel portion. The solid gel portion consists essentially of moieties of an acrylamide as a monomer, a bisacrylamide as a crosslinker, an initiator, an accelerator, a moisture absorbing agent, and an antimicrobial agent. Each ingredient is described herein.

The liquid portion comprises water, and is selected from a group consisting of water, a toning water, an essence water, and any combination thereof. The liquid portion is embedded and distributed within the solid gel portion. The hydrogel layer has covalent crosslinks as a single type of crosslinking structure. The hydrogel layer has a single-layer structure, and the skincare product has no other layer in addition to the hydrogel layer. The hydrogel layer is configured to be applied directly to skin of a subject such as a human being (e.g., a woman). The hydrogel layer provides desired adhesion to a skin surface and can be also peeled off if needed.

In some embodiments, the moisture absorbing agent is selected from the group consisting of calcium sulfate, calcium chloride, potassium chloride, any hydrates thereof, and any combination thereof. The antimicrobial agent is selected from the group consisting of zinc oxide, titanium oxide, and any combination thereof. In some embodiments, the initiator is ammonium persulfate and the accelerator is N,N'-methylenebis(acrylamide) (MBAA).

The base polymer in the hydrogel layer is polyacrylamide (PAM). No other base ingredient such as alginates for a dual network hydrogel is used. In some embodiments, the hydrogel does not include poly(N-isopropylacrylamide) (PNIPAM) or polyvinyl alcohol (PVA) for forming dual network. Poly(N-isopropylacrylamide) (PNIPAM) by itself may be used as the base polymer for the hydrogel.

The monomer curative such as N,N'-methylenebis(acrylamide) (MBAA) may be used as a crosslinker. A crosslinking accelerator and/or a photoinitiator may be used.

In some embodiments, the solid gel portion comprises 50%-80% of the acrylamide, 0.1%-1% of the bisacrylamide, 1%-8% of the initiator, 0.1% to 1% of the accelerator, 0.1%-20% of the moisture absorbing agent, and 0.1%-25% of the antimicrobial agent, based on corresponding moieties and a total weight of the solid gel portion on a dry weight basis.

In some embodiments, in the skincare product, the acrylamide and the bisacrylamide provide the polymer matrix of the hydrogel.

The hydrogel is configured to provide directional evaporative cooling.

The hydrogel layer has any suitable thickness, for example, in a range of from 0.5 mm to 1 cm (e.g., from 1 mm to 10 mm).

The present disclosure provides a wearable skincare and cooling solution that harnesses passive cooling, more specifically, the dissipation of heat via evaporation of water out of a hydrogel. Hydrogel-based evaporative cooling mimics perspiration of mammals. The hydrogel in the skincare product provided in the present disclosure also utilizes unique combination of polymer or polymers and additives and/or fillers.

Figure 1:
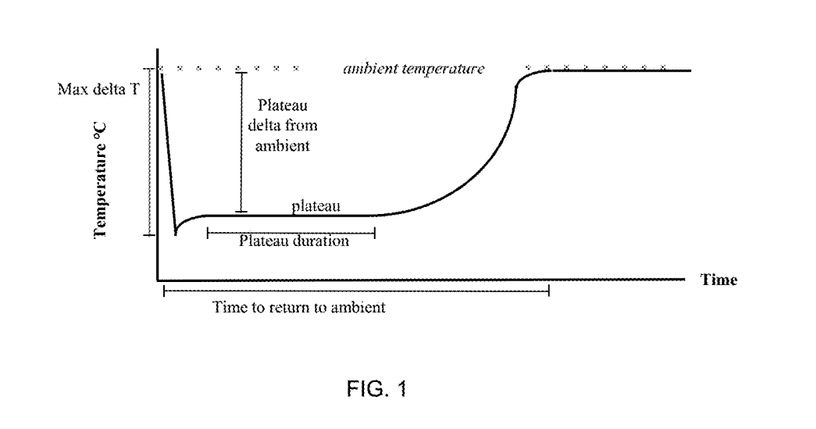
FIG. 1 illustrates the cooling effect of an exemplary skincare product such as a patch provided in the present disclosure.

When not in use, the skincare product such as a mask or patch is stored in a sealed insulating pouch to prevent dehydration of the hydrogel; it does not require refrigeration. To use the patch, one removes it from the packaging and presses the patch on one's body for adhesion. Upon contact with skin (temperature ~36° C.), water evaporates out of the hydrogel and into the ambient environment, effectively drawing heat away from the body and reducing skin temperature. In a time period such as the first 30 minutes of use, the patch achieves a temperature reduction of a maximum temperature delta (e.g., ~8.5° C.) in the skin of contact (as illustrated in FIG. 1). The temperature reduction effect may maintain a plateau and then decreases in magnitude over time to provide graduated and safe cooling for a certain total time until the hydrogel is dried out. To re-use the patch, one rehydrates the hydrogel by adding liquid (such as water or a composition for the liquid portion as described herein) to the gel surface. The skincare product such as a patch or mask may also absorb moisture from air or in a moisture chamber for hydration during storage before re-use. The patch can then be placed on the human body for another cycle of cooling. The patch can be used for a plurality of times, for example, up to 30 cycles of cooling, before it is disposed of due to wear and tear.

The skincare product such as mask or pad provided in the present disclosure is thin, and contours to the human body. The hydrogel layer in contact with skin is biocompatible. The water-based nature of the material and its independence from refrigeration makes it particularly suitable for travel.

Sometimes the moisture absorbing additive such as $CaCl_2$ and KCl is water soluble. With water vapor solvents/sorbents, hygroscopic salts with high water affinity can be dissolved in hydrated hydrogel. For example, $CaCl_2$ is exothermic when dissolved, and could absorb heat during endothermic recrystallization when water evaporates out of the hydrogel.

In some embodiments, the base polymer in the hydrogel layer is polyacrylamide (PAM), without any alginates such as calcium alginate or sodium alginate.

The antimicrobial additive or filler comprises zinc oxide. Zinc oxide is a preferred filler to be used because of its thermal and antibacterial properties.

The skincare product provided herein has good mechanical properties such as good toughness while also having good adhesion. No insulation supporting layer is needed. No adhesive layer is needed. The exemplary skincare product can be applied onto a surface such as a skin. The surface can be wet or dry. Before used, the skincare product is stored in sealed packaging at room temperature. No refrigeration is needed. It can be taken out of the enclosure and can be reused multiple times before disposal.

The skincare product may be in any shape and at any size. For example, the skincare product may be rectangular, square, circular, oval or any other regular or irregular shape. It may also contain one or more holes, cuts, cavities, or depressions, for example, to fit with a face.

A hydrogel layer having less than 50% of the liquid portion comprising water is also provided in the present disclosure. Such a hydrogel layer can be soaked with water or exposed to moisture to have the liquid portion comprising water above 50% to be a desirable level such as 50%-95% or 80%-96%.

In another aspect, the present disclosure provides a pack (or called packed product) comprising an enclosure and the skin skincare product enclosed therein. The skincare product as described herein disposed inside the enclosure. Such a skincare product may be in a form including, but not limited to a mask, a pad, a patch, a film or any combination thereof. The skincare product is reusable.

In another aspect, the present disclosure provides a method of making the skincare product as described herein. The method comprises the steps of making each component and combining together to form the skincare product. Such a method comprises mixing at least two portions of sols as described herein.

In some embodiments, the method of making the skincare product as described herein comprises mixing at least two portions of sols, which a first portion of sol comprising the acrylamide, and a second portion of sol comprising the bisacrylamide. Each sol comprising water. The method may further comprise mixing a third portion of sol, which comprises the antimicrobial agent.

The present disclosure also provides a method of making the packed product as described herein.

In another aspect, the present disclosure provides a method of using the skincare product as described herein. For example, such a method comprises at least one step of applying the skincare product onto a surface such as skin or a body part of a subject. Such a subject is a human being, for example, any person with skin care needed, an athlete, or a patient.

The mechanism of action is directional evaporative cooling to mimic and augment sweating. Upon contact with human skins (or another warm surface), water evaporates out of the hydrogel matrix into the ambient environment, thus reducing the temperature of the skin in contact. The cooling effect ends when the hydrogel matrix is desiccated. The material can be rehydrated with water or a composition for the liquid portion for a next cycle of cooling. The hydrogel material can withstand a plurality of cycles, such as 30 cycles of cooling prior to disposal. It can be stored at ambient temperature and atmosphere or a moisture chamber or a sealed insulating pouch or a closed container.

The skincare product provided in the present disclosure can be used by a healthy human being such as a woman. The toning or essence water in the skincare product provides skincare benefits while also providing cooling effect.

Examples

The samples below were prepared using the following procedures: Solution A (or sol A) and Solution B (or sol B) were mixed in 4:1 ratio by volume, and the desired volume of Solution C (or sol C) containing additives such as zinc oxide was added. The solutions were directly poured into closed molds of the desired shape of the skincare products such as masks. Gelation occurred within 12 hours in the molds at room temperature. The skincare product such as mask can then be removed from the mold for usage. The skincare products such as masks had a thickness in a range of from 1 mm to 3 mm.

Sol A comprises acrylamide in a range of 12.95-17.45 wt. % of Sol A (equivalent to 9-14.0 wt. % overall gel) and a liquid portion comprising water in a range of 82.5-87 wt. % of Sol A. The water portion is divided into facial toning or essence water (0-28 wt. % overall gel) and deionized water (remaining water content in Sol A). In the formulations presented in Tables 1-12, "water" refers to the liquid portion comprising water including deionized water plus facial toning or essence water. Sol A further includes TEMED of 0.05 wt. % of Sol A (equivalent to 0.03-0.04 wt. % overall gel).

Sol B comprises 0.109 wt. % N,N'-methylenebis(acrylamide) solution in a range of 22.5-31.4 wt % of Sol B (equivalent to 0.005-0.007 wt. % overall gel), 1.09 wt % ammonium persulfate solution in a range of 37.5-60 wt % of Sol B (equivalent to 0.08-0.11 wt % overall gel), and 6.06 wt % $CaSO_4$ ½$H_2O$ solution in a range of 13.7-40 wt % of Sol B (equivalent to 0.15-0.48 wt % overall gel).

Sol C includes zinc oxide in a range of 0-5 wt % of total mass of the skincare product, which is a mask.

The water content in total in the overall gel ranges 84.3-89.1 wt % in the samples described herein.

Instruction to use the skincare product includes the following procedures: the skincare product such as a mask is stored at room temperature in a closed container. A small amount of facial toner, skincare essence, or regular water is dropped on the surface of the mask prior to usage for wetting purposes. The mask is then applied to the desired location on the face or neck. After usage, the mask is rinsed with water for cleaning, and is returned to its container for storage. The mask can be reused for another cycle of cooling after rehydration (apply more water, toner, or essence). The mask lasts for 30 cooling cycles and can be stored for one month, and can be used daily for one month before discarding.

Testing Methods: The testing conditions included controlled temperature chamber set at 37° C. and relative humidity 30-60%. Sample thickness was 2.5 mm. Samples were placed on temperature probes with data loggers on acrylic plates (acrylic model for human skin with similar thermal resistances). As illustrated in FIG. 1, the temperature drop ($\Delta$) is a drop in temperature after sample placement, subtracted from temperature at t=0 (acrylic plate only). The plateau is the flat portion of the S-shaped temperature curve, after the initial temperature drop, during which the sample's cooling performance is relatively constant.

The formulations and experimental data are shown in Tables 1-12.

1. Effect of Alginate

Table 1 shows the formulations with and without alginate for forming double network and the related testing results. Sodium Alginate ("alg") was used. Table 2 shows the formulations excluding the water including facial toning and essence water. Example 1 ("Ex. 1") can be considered as a comparative example. With a decreasing alginate content, gel toughness decreases and stickiness increases. Reducing the percentage of the alginate improves cooling magnitude and gel adhesion to skin. Therefore, in the skincare product provided in this disclosure, it is preferable not to use any alginate.

TABLE 1

| Formulation | Ex. 1<br>14.95 AAM/<br>2.5 alg | Ex. 2<br>16.95 AAM/<br>0.5 alg | Ex. 3<br>17.2 AAM/<br>0.25 alg | Ex. 4<br>17.45 AAM/<br>0 alg |
|---|---|---|---|---|
| Sol. A (by wt. % or part in Sol. A) | | | | |
| AAM | 14.95 | 16.95 | 17.2 | 17.45 |
| Sodium Alginate | 2.5 | 0.5 | 0.25 | 0 |
| Water | 82.5 | 82.5 | 82.5 | 82.5 |
| TEMED | 0.05 | 0.05 | 0.05 | 0.05 |
| Sol. A (% total gel) | 80 | 80 | 80 | 80 |
| Sol. B (by wt. % or part in Sol. B) | | | | |
| MBAA | 0.034 | 0.034 | 0.034 | 0.034 |
| Ammonium persulfate | 0.57 | 0.57 | 0.57 | 0.57 |
| $CaSO_4$ ½$H_2O$ | 1 | 1 | 1 | 1 |
| Water | 98.4 | 98.4 | 98.4 | 98.4 |
| Sol. B (% total gel) | 20 | 20 | 20 | 20 |
| Overall Percentages in Gel | | | | |
| AAM | 12.0 | 13.6 | 13.8 | 14.0 |
| Sodium Alginate | 2 | 0.4 | 0.2 | 0 |
| Water | 85.7 | 85.7 | 85.7 | 85.7 |
| TEMED | 0.04 | 0.04 | 0.04 | 0.04 |
| MBAA | 0.007 | 0.007 | 0.007 | 0.007 |
| Ammonium persulfate | 0.11 | 0.11 | 0.11 | 0.11 |
| $CaSO_4$ ½$H_2O$ | 0.20 | 0.20 | 0.20 | 0.20 |

TABLE 1-continued

| Formulation | Ex. 1<br>14.95 AAM/<br>2.5 alg | Ex. 2<br>16.95 AAM/<br>0.5 alg | Ex. 3<br>17.2 AAM/<br>0.25 alg | Ex. 4<br>17.45 AAM/<br>0 alg |
|---|---|---|---|---|
| Properties | | | | |
| Max. Delta T (° C.) | 10.7 | 11.7 | 12.4 | 14.2 |
| Plateau Duration (mins) | 240 | 420 | 390 | 180 |
| Plateau Delta from Ambient (° C.) | 9 | 7 | 10 | 11.5 |
| Time to return to ambient temp(mins) | 480 | 660 | 780 | 330 |
| % Relative Humidity | 29 | 45 | 43 | 43 |
| Material Characterization | with decreasing alginate content, gel toughness decreases and stickiness increases | | | |

TABLE 2

| Formulation | Ex. 1<br>68 AAM/11 alg | Ex. 2<br>78 AAM/2 alg | Ex. 3<br>79 AAM/1 alg | Ex. 4<br>80 AAM/0 alg |
|---|---|---|---|---|
| Part A (by wt. % in Part A) | | | | |
| AAM | 85.4 | 96.9 | 98.3 | 99.7 |
| Sodium Alginate | 14.3 | 2.9 | 1.4 | 0.0 |
| TEMED | 0.3 | 0.3 | 0.3 | 0.3 |
| Part A (% total gel) | 80 | 80 | 80 | 80 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4 \cdot \frac{1}{2}H_2O$ | 62.3 | 62.3 | 62.3 | 62.3 |
| Part B (% total gel) | 20 | 20 | 20 | 20 |
| Overall Percentages in Gel | | | | |
| AAM | 68.3 | 77.5 | 78.6 | 79.8 |
| Sodium Alginate | 11.4 | 2.3 | 1.1 | 0.0 |
| TEMED | 0.23 | 0.23 | 0.23 | 0.23 |
| MBAA | 0.42 | 0.42 | 0.42 | 0.42 |
| Ammonium persulfate | 7.1 | 7.1 | 7.1 | 7.1 |
| $CaSO_4 \cdot \frac{1}{2}H_2O$ | 12.5 | 12.5 | 12.5 | 12.5 |

2. Effect of Monomer

Table 3 shows the formulations with different monomers such as acrylamide (AAM) and N-isopropylacrylamide (NIPAM). Table 4 shows the formulations excluding the water including facial toning and essence water. PNIPAM, as a thermoresponsive polymer, has a larger initial delta T than PAM but its cooling performance does not last as long. Double networks of PAM with PNIPAM or PAM with PVA exhibit a smaller cooling magnitude than PAM alone.

TABLE 3

| Formulation | Ex. 5<br>PAM | Ex. 6<br>PNIPAM | Ex. 7<br>PAM-<br>PNIPAM | Ex. 8<br>PAM-PVA |
|---|---|---|---|---|
| Sol. A (by wt. % or part in Sol. A) | | | | |
| AAM | 17.45 | 0 | 14.95 | 15.3 |
| NIPAM | 0 | 17.45 | 2.5 | 0 |
| Poly(vinyl) alcohol, hydrolyzed | 0 | 0 | 0 | 1.25 |
| Water | 82.5 | 82.5 | 82.5 | 83.4 |
| TEMED | 0.05 | 0.05 | 0.05 | 0.04 |
| Sol. A (% total gel) | 80 | 80 | 80 | 80 |
| Sol. B (by wt. % or part in Sol. B) | | | | |
| MBAA | 0.034 | 0.034 | 0.034 | 0.034 |
| Ammonium persulfate | 0.57 | 0.57 | 0.57 | 0.57 |
| $CaSO_4 \cdot \frac{1}{2}H_2O$ | 1 | 1 | 1 | 1 |
| Water | 98.4 | 98.4 | 98.4 | 98.4 |
| Sol. B (% total gel) | 20 | 20 | 20 | 20 |
| Overall Percentages in Gel | | | | |
| AAM | 14.0 | 0.0 | 12.0 | 12.2 |
| NIPAM | 0 | 14.0 | 2 | 0 |
| Poly(vinyl) alcohol, hydrolyzed | 0 | 0 | 0 | 1 |
| Water | 85.7 | 85.7 | 85.7 | 86.4 |
| TEMED | 0.04 | 0.04 | 0.04 | 0.04 |
| MBAA | 0.007 | 0.007 | 0.007 | 0.007 |
| Ammonium persulfate | 0.11 | 0.11 | 0.11 | 0.11 |
| $CaSO_4 \cdot \frac{1}{2}H_2O$ | 0.20 | 0.20 | 0.20 | 0.20 |
| Properties | | | | |
| Max. Delta T (° C.) | 12.3 | 13.1 | 10.2 | 11.1 |
| Plateau Duration (mins) | 210 | | 120 | 330 |
| Plateau Delta from Ambient (° C.) | 9 | No plateau | 9.5 | 9.5 |
| Time to return to ambient temp(mins) | 660 | | | 660 |
| % Relative Humidity | 51 | 53 | 50 | 51 |
| Material Characterization | | film not fully solidified | | |

TABLE 4

| Formulation | Ex. 5<br>PAM | Ex. 6<br>PNIPAM | Ex. 7<br>PAM-<br>PNIPAM | Ex. 8<br>PAM-PVA |
|---|---|---|---|---|
| Part A (by wt. % in Part A) | | | | |
| AAM | 99.7 | 0.0 | 85.4 | 92.2 |
| NIPAM | 0.0 | 99.7 | 14.3 | 0.0 |
| Poly(vinyl) alcohol, hydrolyzed | 0.0 | 0.0 | 0.0 | 7.5 |

TABLE 4-continued

| Formulation | Ex. 5 PAM | Ex. 6 PNIPAM | Ex. 7 PAM-PNIPAM | Ex. 8 PAM-PVA |
|---|---|---|---|---|
| TEMED | 0.3 | 0.3 | 0.3 | 0.3 |
| Part A (% total gel) | 80 | 80 | 80 | 80 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4$ ½$H_2O$ | 62.3 | 62.3 | 62.3 | 62.3 |
| Part B (% total gel) | 20 | 20 | 20 | 20 |
| Overall Percentages in Gel | | | | |
| AAM | 79.8 | 0.0 | 68.3 | 73.8 |
| NIPAM | 0.0 | 79.8 | 11.4 | 0.0 |
| Poly(vinyl) alcohol, hydrolyzed | 0.0 | 0.0 | 0.0 | 6.0 |
| TEMED | 0.23 | 0.23 | 0.23 | 0.21 |
| MBAA | 0.42 | 0.42 | 0.42 | 0.42 |
| Ammonium persulfate | 7.1 | 7.1 | 7.1 | 7.1 |
| $CaSO_4$ ½$H_2O$ | 12.5 | 12.5 | 12.5 | 12.5 |

3. Effect of Moisture Absorbing Agent

Table 5 shows the formulations with different levels of calcium sulfate as a moisture absorbing agent. Table 6 shows the formulations excluding the water including facial toning and essence water. Increasing $CaSO_4$ content increases cooling magnitude and gel adhesion to skin, up to a certain level. However, with the content of calcium sulfate above a certain level, the cooling duration decreases. Up to 15% of the concentration of $CaSO_4$ by the dry weight of the gel portion, cooling duration increases with an increase in the concentration of $CaSO_4$; past 15% of the concentration of $CaSO_4$, cooling duration decreases as the concentration of CaSO4 further increases.

TABLE 5

| Formulation | Ex. 9 82.5% water - 1 $CaSO_4$ | Ex. 10 82.5% water - 1.2 $CaSO_4$ | Ex. 11 85% water - 1.8 $CaSO_4$ | Ex. 12 85% water - 2.1 $CaSO_4$ | Ex. 13 85% water - 2.4 $CaSO_4$ |
|---|---|---|---|---|---|
| Sol. A (by wt. % or part in Sol. A) | | | | | |
| AAM | 17.45 | 17.45 | 14.95 | 14.95 | 14.95 |
| Water | 82.5 | 82.5 | 85 | 85 | 85 |
| TEMED | 0.05 | 0.05 | 0.05 | 0.05 | 0.05 |
| Sol. A (% total gel) | 80 | 80 | 80 | 80 | 80 |
| Sol. B (by wt. % or part in Sol. B) | | | | | |
| MBAA | 0.034 | 0.033 | 0.029 | 0.027 | 0.025 |
| Ammonium persulfate | 0.57 | 0.55 | 0.48 | 0.48 | 0.41 |
| $CaSO_4$ ½$H_2O$ | 1 | 1.2 | 1.8 | 2.1 | 2.4 |
| Water | 98.4 | 98.2 | 97.7 | 97.4 | 97.2 |
| Sol. B (% total gel) | 20 | 20 | 20 | 20 | 20 |
| Overall Percentages in Gel | | | | | |
| AAM | 14.0 | 14.0 | 12.0 | 12.0 | 12.0 |
| Water | 85.7 | 85.6 | 87.5 | 87.5 | 87.4 |
| TEMED | 0.04 | 0.04 | 0.04 | 0.04 | 0.04 |
| MBAA | 0.007 | 0.007 | 0.006 | 0.005 | 0.005 |
| Ammonium persulfate | 0.11 | 0.11 | 0.10 | 0.10 | 0.08 |
| $CaSO_4$ ½$H_2O$ | 0.20 | 0.24 | 0.36 | 0.42 | 0.48 |
| Properties | | | | | |
| Max. Delta T (° C.) | 12 | 12.7 | 10.7 | 10.3 | 11.7 |
| Plateau Duration (mins) | 120 | 150 | 360 | 270 | 240 |
| Plateau Delta from Ambient (° C.) | 9 | 10 | 9 | 9 | 10 |
| Time to return to ambient temp(mins) | 540 | 540 | 660 | 690 | 660 |
| % Relative Humidity | 53 | 53 | 61 | 59 | 61 |
| Material Characterization | Increasing $CaSO_4$ increases the gel stickiness | | | | |

TABLE 6

| Formulation | Ex. 9<br>12.5 CaSO$_4$ | Ex. 10<br>13.5 CaSO$_4$ | Ex. 11<br>15.6 CaSO$_4$ | Ex. 12<br>16.1 CaSO$_4$ | Ex. 13<br>16.9 CaSO$_4$ |
|---|---|---|---|---|---|
| Part A (by wt. % in Part A) | | | | | |
| AAM | 99.71 | 99.71 | 99.67 | 99.67 | 99.67 |
| TEMED | 0.29 | 0.29 | 0.33 | 0.33 | 0.33 |
| Part A (% total gel) | 80 | 80 | 80 | 80 | 80 |
| Part B (by wt. % in Part B) | | | | | |
| MBAA | 2.1 | 1.9 | 1.3 | 1.0 | 0.9 |
| Ammonium persulfate | 35.5 | 30.8 | 20.8 | 18.4 | 14.5 |
| CaSO$_4$ ½H$_2$O | 62.3 | 67.3 | 78.0 | 80.6 | 84.7 |
| Part B (% total gel) | 20 | 20 | 20 | 20 | 20 |

TABLE 6-continued

| Formulation | Ex. 9<br>12.5 CaSO$_4$ | Ex. 10<br>13.5 CaSO$_4$ | Ex. 11<br>15.6 CaSO$_4$ | Ex. 12<br>16.1 CaSO$_4$ | Ex. 13<br>16.9 CaSO$_4$ |
|---|---|---|---|---|---|
| Overall Percentages in Gel | | | | | |
| AAM | 79.8 | 79.8 | 79.7 | 79.7 | 79.7 |
| TEMED | 0.23 | 0.23 | 0.27 | 0.27 | 0.27 |
| MBAA | 0.42 | 0.37 | 0.25 | 0.21 | 0.18 |
| Ammonium persulfate | 7.1 | 6.2 | 4.2 | 3.7 | 2.9 |
| CaSO$_4$ ½H$_2$O | 12.5 | 13.5 | 15.6 | 16.1 | 16.9 |

4. Effect of Antimicrobial Agent

Table 7 shows the formulations with different levels of zinc oxide as an antimicrobial agent. Table 8 shows the formulations excluding the water portion including facial toning and essence water. Adding zinc oxide does not compromise cooling performance. Adding ZnO to 2 wt. % in total of the gel increases gel stiffness; past a certain saturation point, for example, with 5 wt. % ZnO in total of the gel (corresponding to 25% ZnO in the solid gel portion on dry weight basis), decreases gel integrity.

TABLE 7

| Formulation | Ex. 1<br>14.95 AAM/<br>2.5 alg | Ex. 14<br>14.95 AAM/<br>2.5 alg/<br>1% ZnO | Ex. 15<br>14.95 AAM/<br>2.5 alg/2%<br>ZnO | Ex. 16<br>14.95 AAM/<br>2.5 alg/5%<br>ZnO |
|---|---|---|---|---|
| Sol. A (by wt. % in Sol. A) | | | | |
| AAM | 14.95 | 14.95 | 14.95 | 14.95 |
| Sodium Alginate | 2.5 | 2.5 | 2.5 | 2.5 |
| Water | 82.5 | 82.5 | 82.5 | 82.5 |
| TEMED | 0.05 | 0.05 | 0.05 | 0.05 |
| Sol. A (% total gel) | 80 | 76 | 72 | 60 |
| Sol. B (by wt. % in Sol. B) | | | | |
| MBAA | 0.034 | 0.034 | 0.034 | 0.034 |
| Ammonium persulfate | 0.57 | 0.57 | 0.57 | 0.57 |
| CaSO$_4$ ½H$_2$O | 1 | 1 | 1 | 1 |
| Water | 98.4 | 98.4 | 98.4 | 98.4 |
| Sol. B (% total gel) | 20 | 19 | 18 | 15 |
| Sol. C (by wt. % in Sol. C) | | | | |
| Zinc oxide | | 20 | 20 | 20 |
| Water | | 80 | 80 | 80 |
| Sol. C (% total gel) | 0 | 5 | 10 | 25 |
| Overall Percentages in Gel | | | | |
| AAM | 12.0 | 11.4 | 10.8 | 9.0 |
| Sodium Alginate | 2 | 1.9 | 1.8 | 1.5 |
| Water | 85.7 | 85.4 | 85.1 | 84.3 |
| TEMED | 0.04 | 0.04 | 0.04 | 0.03 |
| Zinc oxide | 0 | 1 | 2 | 5 |
| MBAA | 0.007 | 0.006 | 0.006 | 0.005 |
| Ammonium persulfate | 0.11 | 0.11 | 0.10 | 0.09 |
| CaSO$_4$ ½H$_2$O | 0.20 | 0.19 | 0.18 | 0.15 |
| Properties | | | | |
| Max. Delta T (° C.) | 10.7 | 10.9 | 10.9 | 10.7 |
| Plateau Duration (mins) | 240 | 480 | 180 | |
| Plateau Delta from Ambient (° C.) | 9 | 7.5 | 9.5 | 7 |

TABLE 7-continued

| Formulation | Ex. 1 14.95 AAM/ 2.5 alg | Ex. 14 14.95 AAM/ 2.5 alg/ 1% ZnO | Ex. 15 14.95 AAM/ 2.5 alg/2% ZnO | Ex. 16 14.95 AAM/ 2.5 alg/5% ZnO |
|---|---|---|---|---|
| Time to return to ambient temp(mins) | 480 | 660 | 450 | |
| % Relative Humidity | 29 | 43 | 29.5 | 34 |
| Material Characterization | | | white color, chalky, stiffer than 0% ZnO | very sticky, less integrity |

TABLE 8

| Formulation | Ex. 1 0 ZnO | Ex. 14 5 ZnO | Ex. 15 10 ZnO | Ex. 16 25 ZnO |
|---|---|---|---|---|
| Part A (by wt. % in Part A) | | | | |
| AAM | 85.4 | 85.4 | 85.4 | 85.4 |
| Sodium Alginate | 14.3 | 14.3 | 14.3 | 14.3 |
| TEMED | 0.3 | 0.3 | 0.3 | 0.3 |
| Part A (% total gel) | 80 | 76 | 72 | 60 |
| Part B (by wt. % in Part B) | | | | |
| MBAA | 2.1 | 2.1 | 2.1 | 2.1 |
| Ammonium persulfate | 35.5 | 35.5 | 35.5 | 35.5 |
| $CaSO_4 \cdot \frac{1}{2}H_2O$ | 62.3 | 62.3 | 62.3 | 62.3 |
| Part B (% total gel) | 20 | 19 | 18 | 15 |
| Part C (by wt. % in Part C) | | | | |
| Zinc oxide | | 100 | 100 | 100 |
| Part C (% total gel) | 0 | 5 | 10 | 25 |
| Overall Percentages in Gel | | | | |
| AAM | 68.3 | 64.9 | 61.5 | 51.3 |
| Sodium Alginate | 11.4 | 10.9 | 10.3 | 8.6 |
| TEMED | 0.23 | 0.22 | 0.21 | 0.17 |
| Zinc oxide | 0 | 5 | 10 | 25 |
| MBAA | 0.42 | 0.40 | 0.38 | 0.32 |
| Ammonium persulfate | 7.1 | 6.8 | 6.4 | 5.3 |
| $CaSO_4 \cdot \frac{1}{2}H_2O$ | 12.5 | 11.8 | 11.2 | 9.4 |

5. Effect of Water

Table 9 shows the formulations with different "water" content, i.e., the content of the liquid portion comprising water. Table 10 shows the formulations excluding the water including facial toning and essence water. Increasing water content up to 86% (in Sol A) increases cooling magnitude. When the water content is above 86%, cooling magnitude decreases. Increasing water content decreases gel integrity and increases gel stickiness and adhesion to skin.

TABLE 9

| Formulation | Ex. 17 82.5% water- 16.3 $CaSO_4$ | Ex. 18 83.5% water- 16.3 $CaSO_4$ | Ex. 19 85% water- 16.3 $CaSO_4$ | Ex. 20 85% water- 30 $CaSO_4$ | Ex. 21 86% water- 30 $CaSO_4$ | Ex. 22 87% water- 30 $CaSO_4$ |
|---|---|---|---|---|---|---|
| Sol. A (by wt. % or part in Sol. A) | | | | | | |
| AAM | 17.45 | 16.45 | 14.95 | 14.95 | 13.95 | 12.95 |
| Water | 82.5 | 83.5 | 85 | 85 | 86 | 87 |
| TEMED | 0.05 | 0.05 | 0.05 | 0.05 | 0.05 | 0.05 |
| Sol. A (% total gel) | 80 | 80 | 80 | 80 | 80 | 80 |
| Sol. B (by wt. % or part in Sol. B) | | | | | | |
| MBAA | 0.034 | 0.034 | 0.034 | 0.029 | 0.029 | 0.029 |
| Ammonium persulfate | 0.57 | 0.57 | 0.57 | 0.48 | 0.48 | 0.48 |
| $CaSO_4 \cdot \frac{1}{2}H_2O$ | 1 | 1 | 1 | 1.8 | 1.8 | 1.8 |
| Water | 98.4 | 98.4 | 98.4 | 97.7 | 97.7 | 97.7 |
| Sol. B (% total gel) | 20 | 20 | 20 | 20 | 20 | 20 |
| Overall Percentages in Gel | | | | | | |
| AAM | 14.0 | 13.2 | 12.0 | 12.0 | 11.2 | 10.4 |
| Water | 85.7 | 86.5 | 87.7 | 87.5 | 88.3 | 89.1 |
| TEMED | 0.04 | 0.04 | 0.04 | 0.04 | 0.04 | 0.04 |
| MBAA | 0.007 | 0.007 | 0.007 | 0.006 | 0.006 | 0.006 |
| Ammonium persulfate | 0.11 | 0.11 | 0.11 | 0.10 | 0.10 | 0.10 |
| $CaSO_4 \cdot \frac{1}{2}H_2O$ | 0.20 | 0.20 | 0.20 | 0.36 | 0.36 | 0.36 |

TABLE 9-continued

| Formulation | Ex. 17 82.5% water- 16.3 CaSO$_4$ | Ex. 18 83.5% water- 16.3 CaSO$_4$ | Ex. 19 85% water- 16.3 CaSO$_4$ | Ex. 20 85% water- 30 CaSO$_4$ | Ex. 21 86% water- 30 CaSO$_4$ | Ex. 22 87% water- 30 CaSO$_4$ |
|---|---|---|---|---|---|---|
| Properties | | | | | | |
| Max. Delta T (° C.) | 12 | 11.6 | 13.2 | 10.9 | 11.2 | 10.3 |
| Plateau Duration (mins) | 120 | 330 | 150 | 330 | 330 | 300 |
| Plateau Delta from Ambient (° C.) | 9 | 10 | 11.5 | 9 | 10 | 9 |
| Time to return to ambient temp(mins) | 540 | 660 | 330 | 540 | 660 | |
| % Relative Humidity | 53 | 55 | 55 | 54 | 54 | 60 |
| Material Characterization | Increasing water content decreases gel toughness | | | | | |

TABLE 10

| Formulation | Ex. 17 82.5% water- 12.5 CaSO$_4$ | Ex. 18 83.5% water- 12.5 CaSO$_4$ | Ex. 19 85% water- 12.5 CaSO$_4$ | Ex. 20 85% water- 15.6 CaSO$_4$ | Ex. 21 86% water- 15.6 CaSO$_4$ | Ex. 22 87% water- 15.6 CaSO$_4$ |
|---|---|---|---|---|---|---|
| Part A (by wt. % in Part A) | | | | | | |
| AAM | 99.71 | 99.70 | 99.67 | 99.67 | 99.64 | 99.62 |
| TEMED | 0.29 | 0.30 | 0.33 | 0.33 | 0.36 | 0.38 |
| Part A (% total gel) | 80 | 80 | 80 | 80 | 80 | 80 |
| Part B (by wt. % in Part B) | | | | | | |
| MBAA | 2.1 | 2.1 | 2.1 | 1.3 | 1.3 | 1.3 |
| Ammonium persulfate | 35.5 | 35.5 | 35.5 | 20.8 | 20.8 | 20.8 |
| CaSO$_4$ ½H$_2$O | 62.3 | 62.3 | 62.3 | 78.0 | 78.0 | 78.0 |
| Part B (% total gel) | 20 | 20 | 20 | 20 | 20 | 20 |
| Overall Percentages in Gel | | | | | | |
| AAM | 79.8 | 79.8 | 79.7 | 79.7 | 79.7 | 79.7 |
| TEMED | 0.23 | 0.24 | 0.27 | 0.27 | 0.29 | 0.31 |
| MBAA | 0.42 | 0.42 | 0.42 | 0.25 | 0.25 | 0.25 |
| Ammonium persulfate | 7.1 | 7.1 | 7.1 | 4.2 | 4.2 | 4.2 |
| CaSO$_4$ ½H$_2$O | 12.5 | 12.5 | 12.5 | 15.6 | 15.6 | 15.6 |

6. Effect of Toner

Table 11 shows the formulations with different levels of facial toner solution. Table 12 shows the formulations excluding the water including facial toning and essence water. Adding facial toner decreases gel toughness. However, there is no observed decrease in cooling performance.

TABLE 11

| Formulation | Ex. 23 82.5% water- 16.3 CaSO$_4$ | Ex. 24 82.5% water- 16.3 CaSO$_4$- 28% toner | Ex. 25 85% water- 35 CaSO$_4$ | Ex. 26 85% water-35 CaSO$_4$-5% toner |
|---|---|---|---|---|
| Sol. A (by wt. % or part in Sol. A) | | | | |
| AAM | 17.45 | 17.45 | 14.95 | 14.95 |
| Water | 82.5 | 47.5 | 85 | 78.75 |
| Facial Toner | 0 | 35 | 0 | 6.25 |
| TEMED | 0.05 | 0.05 | 0.05 | 0.05 |
| Sol. A (% total gel) | 80 | 80 | 80 | 80 |
| Sol. B (by wt. % or part in Sol. B) | | | | |
| MBAA | 0.034 | 0.034 | 0.027 | 0.027 |
| Ammonium persulfate | 0.57 | 0.57 | 0.48 | 0.48 |
| CaSO$_4$ ½H$_2$O | 1 | 1 | 2.1 | 2.1 |
| Water | 98.4 | 98.4 | 97.4 | 97.4 |
| Sol. B (% total gel) | 20 | 20 | 20 | 20 |

TABLE 11-continued

| Formulation | Ex. 23 82.5% water- 16.3 CaSO$_4$ | Ex. 24 82.5% water- 16.3 CaSO$_4$- 28% toner | Ex. 25 85% water- 35 CaSO$_4$ | Ex. 26 85% water-35 CaSO$_4$-5% toner |
|---|---|---|---|---|
| Overall Percentages in Gel | | | | |
| AAM | 14.0 | 14.0 | 12.0 | 12.0 |
| Water | 85.7 | 57.7 | 87.5 | 82.5 |
| Facial toner | 0 | 28 | 0 | 5 |
| TEMED | 0.04 | 0.04 | 0.04 | 0.04 |
| MBAA | 0.007 | 0.007 | 0.005 | 0.005 |
| Ammonium persulfate | 0.11 | 0.11 | 0.10 | 0.10 |
| CaSO$_4$ ½H$_2$O | 0.20 | 0.20 | 0.42 | 0.42 |
| Properties | | | | |
| Max. Delta T (° C.) | 10.6 | 12.9 | 12.9 | 12.0 |
| Plateau Duration (mins) | >120 (time_final = 120) | 60 | 120 | 120 |
| Plateau Delta from Ambient (° C.) | 9.5 | 12.5 | 12.5 | 11.5 |
| Time to return to ambient temp(mins) | | | | |
| % Relative Humidity | 54 | 54 | 45 | 45 |
| Material Characterization | Increasing facial toner content decreases gel toughness | | | |

TABLE 12

| Formulation | Ex. 23 12.5 CaSO$_4$ | Ex. 24 12.5 CaSO$_4$- 53% toner | Ex. 25 16.1 CaSO$_4$ | Ex. 26 16.1 CaSO$_4$- 24% toner |
|---|---|---|---|---|
| Part A (by wt. % in Part A) | | | | |
| AAM | 99.7 | 33.2 | 99.7 | 70.4 |
| Facial Toner | 0 | 67 | 0 | 29 |
| TEMED | 0.29 | 0.10 | 0.33 | 0.24 |
| Part A (% total gel) | 80 | 80 | 80 | 80 |
| Part B (by wt. % in Part B) | | | | |
| MBAA | 2.1 | 2.1 | 1.0 | 1.0 |
| Ammonium persulfate | 35.5 | 35.5 | 18.4 | 18.4 |
| CaSO$_4$ ½H$_2$O | 62.3 | 62.3 | 80.6 | 80.6 |
| Part B (% total gel) | 20 | 20 | 20 | 20 |
| Overall Percentages in Gel | | | | |
| AAM | 79.8 | 26.6 | 79.7 | 56.3 |
| Facial toner | 0 | 53 | 0 | 24 |
| TEMED | 0.23 | 0.08 | 0.27 | 0.19 |
| MBAA | 0.42 | 0.42 | 0.21 | 0.21 |
| Ammonium persulfate | 7.1 | 7.1 | 3.7 | 3.7 |
| CaSO$_4$ ½H$_2$O | 12.5 | 12.5 | 16.1 | 16.1 |

Figure 2:
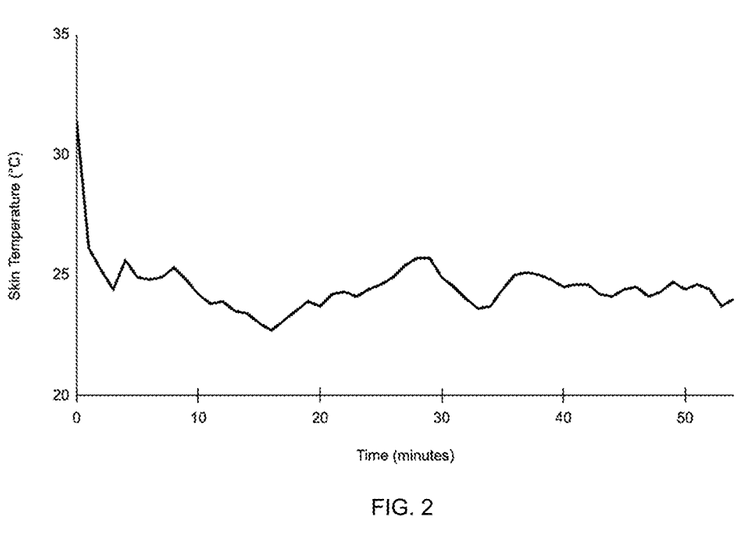
FIG. 2 shows the cooling effect of an experimental example.

FIG. 2 shows experimental data showing cooling effect of one example of hydrogel, which is a single-network PAM hydrogel with infused toner and has a formulation similar to Example 24. A temperature probe was taped to skin and left to calibrate until the reported temperature of the skin surface in contact was constant. Then the data logger was activated to record skin temperature. Immediately after the temperature recording was started, the hydrogel sample (2.0 mm thick) was placed over the skin & temperature probe. As shown in FIG. 2, the sample decreased skin temperature in contact by over eight degree (8° C.) and sustained for at least one hour.

The skincare product provided in this disclosure has many advantages. It provides skincare benefits such as cosmetic effect while also providing cooling effect. It has a single-layer structure and does not need any supporting layer. The hydrogel has good toughness, other mechanical properties, and good adhesion to a surface such as skin. It is easy for use and can be reusable.

Although the subject matter has been described in terms of exemplary embodiments, it is not limited thereto. Rather, the appended claims should be construed broadly, to include other variants and embodiments, which may be made by those skilled in the art.

What is claimed is:

1. A skincare product configured to provide skincare and cooling, wherein the skincare product is in a form selected from the group consisting of a mask, a pad, a patch, and any combination thereof and has single-layer structure a hydrogel layer configured to be directly applied to a skin surface at room temperature, the hydrogel layer comprising:
   at least 50% of a liquid portion based on a total weight of the hydrogel layer; and
   a solid gel portion comprising moieties of an acrylamide as a monomer, a bisacrylamide as a crosslinker, a moisture absorbing agent, and an antimicrobial agent;
   wherein the liquid portion comprises water and is selected from a group consisting of water, a toning water, and an essence water, the liquid portion is embedded and distributed within the solid gel portion,
   wherein the hydrogel layer has covalent crosslinks as the only one type of crosslinking structure in the hydrogel, and
   wherein the solid gel portion comprises 50%-80% of the moieties of the acrylamide, 0.1%-1% of the moieties of the bisacrylamide, 0.1%-20% of the moisture absorbing agent, and 0.1%-25% of the antimicrobial agent, based on a total weight of the solid gel portion on a dry weight basis.

2. The skincare product of claim 1, wherein the moisture absorbing agent is selected from the group consisting of calcium sulfate, calcium chloride, potassium chloride, any hydrates thereof, and any combination thereof.

3. The skincare product of claim 1, wherein the antimicrobial agent is selected from the group consisting of zinc oxide, titanium oxide, and any combination thereof.

4. The skincare product of claim 1, wherein the solid gel portion further comprises moieties from an initiator in a range of from 1% to 8% and an accelerator in a range of from 0.1% to 1%, based on a total weight of the solid gel portion on a dry weight basis.

5. The skincare product of claim 4, wherein the initiator is ammonium persulfate and the accelerator is N,N'-methylenebis(acrylamide) (MBAA).

6. The skincare product of claim 1, wherein the hydrogel layer comprises 80% to 86% of the liquid portion based on the total weight of the hydrogel layer.

7. The skincare product of claim 1, wherein the acrylamide and the bisacrylamide provide a sole polymer in a matrix of the hydrogel layer.

8. The skincare product of claim 1, wherein the hydrogel layer is configured to provide directional evaporative cooling.

9. A skincare product configured to provide skincare and cooling, wherein the skincare product is in a form selected from the group consisting of a mask, a pad, a patch, and any combination thereof and has a single-layer structure being a hydrogel layer configured to be directly applied to a skin surface at room temperature, the hydrogel layer comprising:
50%-95% of a liquid portion based on a total weight of the hydrogel layer; and
a solid gel portion consisting essentially of moieties of an acrylamide as a monomer, a bisacrylamide as a crosslinker, an initiator, an accelerator, a moisture absorbing agent, and an antimicrobial agent;
the liquid portion comprises water and is selected from a group consisting of water, a toning water, and an essence water, the liquid portion is embedded and distributed within the solid gel portion,
the hydrogel layer has covalent crosslinks as the only one type of crosslinking structure in the hydrogel layer, and
the solid gel portion comprises 50%-80% of the moieties of the acrylamide, 0.1%-1% of the moieties of the bisacrylamide, 0.1%-20% of the moisture absorbing agent, and 0.1%-25% of the antimicrobial agent, based on a total weight of the solid gel portion on a dry weight basis.

10. The skincare product of claim 9, wherein the moisture absorbing agent is selected from the group consisting of calcium sulfate, calcium chloride, potassium chloride, any hydrates thereof, and any combination thereof.

11. The skincare product of claim 9, wherein the antimicrobial agent is selected from the group consisting of zinc oxide, titanium oxide, and any combination thereof.

12. The skincare product of claim 9, wherein the initiator is ammonium persulfate and the accelerator is N,N'-methylenebis(acrylamide) (MBAA).

13. The skincare product of claim 9, wherein the acrylamide and the bisacrylamide provide a sole polymer in a matrix of the hydrogel layer.

14. The skincare product of claim 9, wherein the hydrogel layer is configured to provide directional evaporative cooling.

15. A method of making the skincare product of claim 1, comprising mixing at least two portions of sols, the at least two portions of sols comprising a first portion of sol comprising the acrylamide, and a second portion of sol comprising the bisacrylamide, each sol comprising water.

16. The method of claim 15, further comprising mixing a third portion of sol comprising the antimicrobial agent.

17. A pack comprising an enclosure and the skin skincare product of claim 1 enclosed therein.

18. The skincare product of claim 1, wherein the liquid portion is a toning water or an essence water.

19. The skincare product of claim 9, wherein the liquid portion is a toning water or an essence water.

* * * * *